United States Patent [19]

Arco

[11] Patent Number: 4,627,427
[45] Date of Patent: Dec. 9, 1986

[54] UNIVERSAL MEDICAL COVER SHEET AND PROCESS FOR DRAPING

[75] Inventor: Judith A. Arco, Stillwater, Minn.

[73] Assignee: Minnesota Mining and Manufacturing Company, St. Paul, Minn.

[21] Appl. No.: 661,688

[22] Filed: Oct. 17, 1984

[51] Int. Cl.[4] ............................................. A61F 13/00
[52] U.S. Cl. .............................................. 128/132 D
[58] Field of Search ............... 128/132 D, 132 R, 155, 128/165

[56] References Cited

U.S. PATENT DOCUMENTS

| | | | |
|---|---|---|---|
| 3,537,446 | 11/1970 | Rowland | 128/132 D |
| 3,540,441 | 11/1970 | Collins | 128/165 X |
| 3,777,749 | 12/1973 | Collins | 128/132 D |
| 3,799,161 | 3/1974 | Collins | 128/132 D |
| 3,835,851 | 9/1974 | Villari | 128/132 D |
| 3,968,792 | 7/1976 | Small | 128/132 D |
| 3,989,040 | 11/1976 | Lofgren et al. | 128/132 D |
| 4,024,862 | 5/1977 | Collins | 128/132 D |
| 4,051,845 | 10/1977 | Collins | 128/132 D |
| 4,224,935 | 9/1980 | Metelnick | 128/165 X |
| 4,275,719 | 6/1981 | Mayer | 128/132 D |
| 4,308,864 | 1/1982 | Small et al. | 128/132 D |
| 4,336,797 | 6/1982 | Latucca et al. | 128/132 D |
| 4,370,978 | 2/1983 | Palumbo | 128/165 X |

FOREIGN PATENT DOCUMENTS 1395389  5/1975  United Kingdom .

*Primary Examiner*—F. Barry Shay
*Attorney, Agent, or Firm*—Donald M. Sell; James A. Smith; Mary M. Allen

[57] ABSTRACT

An article adaptable for use as a universal medical cover sheet is shown. The article is comprised of draping material and an integrally associated surgical zone and is formed as a closed loop. The loop is dimensioned such that opening of the loop yields a cover sheet having the surgical zone positioned within the draping material so that non-surgical areas of a patient are covered sufficiently for surgical purposes by draping material when the surgical zone is placed to permit access to the surgical site involved in the procedure. The loop is preferably formed so that its outer surface will become the patient surface of the cover sheet resulting upon opening of the loop. It is preferably folded first along longitudinal fold lines and thereafter along transverse fold lines. The folding preferably results in exposure of the surgical zone at an outer surface of the folded loop. Selection of the line along which the loop should be opened for a given procedure is facilitated by providing transverse cut marks on the draping material. In use, the surgical nurse would determine where the loop should be opened, open the loop preferably by cutting with sterile scissors, place the surgical zone on the surgical site involved in the procedure, and then unfold the cover sheet.

19 Claims, 7 Drawing Figures

UNIVERSAL MEDICAL COVER SHEET AND PROCESS FOR DRAPING

FIELD OF THE INVENTION

This invention relates to the field of medical cover sheets. More particularly, the invention relates to an article adaptable for use as a medical cover sheet useful in a variety of different procedures especially surgical procedures.

BACKGROUND OF THE INVENTION

Hospitals currently inventory a large variety of medical cover sheets for use in conventional surgery and other invasive medical procedures. While this invention has particular application for surgical procedures and is described in that context it may be used in medical procedures generally. The cover sheet or cover sheet assembly used for a procedure is dictated by the location and size of the contemplated incision. That is, the sheet or assembly has a fenestration (an opening with or without an adhesive surrounding the opening) or an incise patch (a film with or without adhesive and liner in which the adhesive may incorporate an antimicrobial agent), positioned to permit access to the contemplated surgical site with draping material surrounding the surgical zone to cover the remainder of the patient's body sufficiently to protect the surgical site from contamination by the patient's body or from the surrounding environment. Other cover sheets or cover sheet assemblies have stretchy apertures which are thermoplastic elastomeric films with an opening in the film. These drapes with stretchy apertures are particularly useful for procedures performed on limbs. In use the arm or leg is inserted through the opening of the stretchy aperture while the draping material covers the patient's body and an extremity drape is applied to the limb.

As used throughout the specification and claims the term "surgical zone" will refer to that portion of a medical cover sheet through which the patient's body is accessed for a medical or surgical procedure including fenestrations, incise patches, stretchy apertures and composites made with a fenestration having a film (with or without adhesive) covering all or part of the fenestration.

Today, hospitals stock a variety of cover sheets each having the surgical zone placed at a different position in the sheet. Thus a hospital inventory would include cover sheets with the surgical zone placed near one end for head surgery, placed somewhat removed from one end for chest surgery, placed near the center of the drape for laparotomies as well as drapes with surgical zones positioned farther from the head end of the drape for knee and foot/ankle surgeries.

In addition to stocking a variety of procedure cover sheets having the surgical zone positioned in different portions of the sheet, hospitals typically inventory multiple sizes of smaller sheets which are combined to build a procedure drape assembly having a surgical zone around the surgical site. Additionally, some hospitals stock split sheets or U-shaped sheets two of which can be placed with the split or "U" openings overlapping or abutting to customize location and size of the surgical zone.

Cover sheets which can be used for multiple incision sites have been proposed. U.S. Pat. No. 4,336,797 describes a surgical cover sheet having a main sheet with a fenestration and a frame sheet with a similar fenestration secured to the upper surface of the main sheet. The frame sheet is slidably secured to the main sheet so that moving the frame sheet relative to the main sheet will vary the size and position of the surgical zone. U.S. Pat. No. 3,799,161 describes a surgical cover sheet having a plurality of fenestrations located in the sheet. Each fenestration is covered with a removably secured cover sheet so that the cover sheet positioned over the incision site can be removed while the cover sheets over the remaining fenestrations can be left in place to maintain a sterile barrier during the procedure. Great Britain Pat. No. 1,395,389 discloses a surgical cover sheet having fan folds from at least one longitudinal end to center wherein the first and second folds are smaller than the remaining folds and the second fold is a reverse fold while the third fold is a forward fold. The specification discloses that the sheet may be cut through stacks of folds to create a slit of varying lengths in the longitudinal direction. Additionally, the patent discloses creating a fenestration by making an arcuate cut in a fold of the sheet.

Another concept for providing a surgical cover sheet having utility in more than one type of surgical procedure is shown in U.S. Pat. No. 4,024,862. That patent shows a surgical cover sheet having a fenestration of sufficient size for performing an enlarged surgical procedure. Removably secured to the cover sheet on its upper surface is a flexible frame sheet having a fenestration of a smaller size than the fenestration in the main cover sheet.

Surgical cover sheets used for extremity (leg and arm) surgery frequently are constructed tubularly in the transverse direction with one longitudinal end closed. U.S. Pat. No. 4,308,864 shows a combination of conventional stockinette cover sheet and a closed tubular cover sheet. U.S. Pat. No. 3,989,040 shows a cover sheet which is tubular in the transverse direction and sealed at one longitudinal end. The cover sheet has a fenestration cut as a split in the longitudinal direction from the open end of the tube. The cover sheet has a pressure sensitive adhesive along the edges of the split for securing the sides of the fenestration relative to the surgery site.

Methods of folding cover sheets for convenient and aseptic unfolding and placement are multitudinous. Many cover sheets are folded first along transverse fold lines to reduce the longitudinal dimension of the cover sheet and thereafter along longitudinal fold lines to reduce the transverse dimension. Other cover sheets are folded first along longitudinal fold lines and thereafter along transverse fold lines. U.S. Pat. No. 4,051,865 shows a fold pattern of this latter type.

SUMMARY OF THE INVENTION

The present invention overcomes the need for hospitals to inventory a family or surgical cover sheets having the surgical zone located at different positions within the cover sheet. The present invention provides an article which is adaptable to become a universal medical cover sheet. The article is adaptable for draping those areas of the patient's body not involved in the invasive medical procedure, the non-surgical areas, and for providing a surgical zone for use in an invasive medical procedure. It comprises draping material having opposing side edges of substantially equal length and a surgical zone integrally associated with the draping material. The article is formed in a closed loop and dimensioned such that opening of the loop at a selected point yields a surgical cover sheet wherein the surgical zone is positioned within the draping material so that non-surgical areas of the patient are isolated sufficiently for aseptic purposes by draping material when the surgical zone is placed to permit access to the body area involved in the procedure. According to the present invention the surgical zone is positioned at any point along the loop's length, such that selection and opening along a line spaced at an appropriate distance from the surgical zone permits creation of a surgical cover sheet with the surgical zone at a specific location within the cover sheet's length.

Another aspect of the invention involves forming the loop so that the outer surface of the loop is adapted to become upon opening of the loop the patient surface of the cover sheet, that is the surface of the cover sheet which will contact the patient's body.

Opening of the loop with minimal handling of the draping material is facilitated by reducing the transverse dimension of the article by folding along longitudinal lines of the draping material. Preferably the draping material is folded along longitudinal fold lines from each side inwardly to form two juxtaposed stacks of longitudinal folds stacked on the inside of the closed loop. Most preferably these longitudinal folds are fan folds.

In the preferred construction the surgical zone is substantially rectangular having its longitudinal axis substantially equidistant from the side edges of the draping material.

Determination of the line along which the loop should be opened is facilitated by reducing the longitudinal dimension of the longitudinally folded loop by transverse folding of the article. The transverse folds provide points of reference for determining distance relative to the surgical zone. The transverse folds are preferably fan folds.

Selection for a particular procedure of the line along which the loop is opened is also facilitated by marking the draping material with transverse cut indications spaced at intervals from the surgical zone to facilitate the determination. Thus the draping material can be provided with a cut mark sufficiently removed from the surgical zone to yield upon opening of the loop a cover sheet having the surgical zone positioned appropriately for head surgery. Opening at another cut mark somewhat more removed from the surgical zone yields a surgical cover sheet having the surgical zone positioned appropriately for thoracic surgery. Opening at a cut mark somewhat further removed from the surgical zone yields a cover sheet suitable for laparotomies. A cut mark positioned substantially equidistant from both ends of the surgical zone would yield upon opening a surgical cover sheet having the surgical zone appropriately placed for hip surgery. Additional cut marks could be provided on the draping material for knee surgery and foot/ankle surgery. In the preferred embodiment these transverse cut marks fall on fold lines of the transverse folds.

The surgical zone of the present invention can be any type of surgical zone including fenestrations of any shape and size, incise patches, stretchy apertures, composites and even a slit in the draping material.

In another aspect of the invention, the article is folded to expose at an outside surface the surface of a stretchy aperture or incise patch which will become the patient surface of the aperture or patch when placed to permit access to the body area involved in the procedure. In the case of a stretchy aperture this feature permits inserting the extremity through the aperture prior to unfolding of the cover sheet. In the case of an incise patch this feature permits removing the releasable liner and placement of the incise patch prior to unfolding of the cover sheet.

In the process of the present invention the surgical nurse is provided with a closed loop article comprised of draping material and a surgical zone integrally associated with the draping material. The surgical nurse opens the loop along a line distanced an appropriate length from the surgical zone to create a cover sheet with the surgical zone positioned within the draping material so as to provide lengths of material adequate to sufficiently cover non-surgical areas of a patient when the surgical zone is placed to permit access to the body area involved in the procedure. Next the nurse places the surgical zone to permit access to the involved body area and adequately cover the non-surgical areas of the patient.

In the preferred process of the present invention the surgical nurse determines the distance between the surgical zone placement for the procedure involved and the top (or bottom) of the cover sheet to be formed on opening of the loop. The loop is then opened across a line sufficiently distant from the surgical zone to form a cover sheet wherein the surgical zone is positioned within the draping material so as to provide lengths of draping material adequate to sufficiently cover non-surgical areas when the surgical zone is placed to permit access to the body area involved in the procedure. Thereafter the surgical zone is placed to permit access to the body area involved in the procedure. Then the transverse folds of the draping material are unfolded, and finally the longitudinal folds of the draping material are unfolded.

DETAILED DESCRIPTION

Figure 1:
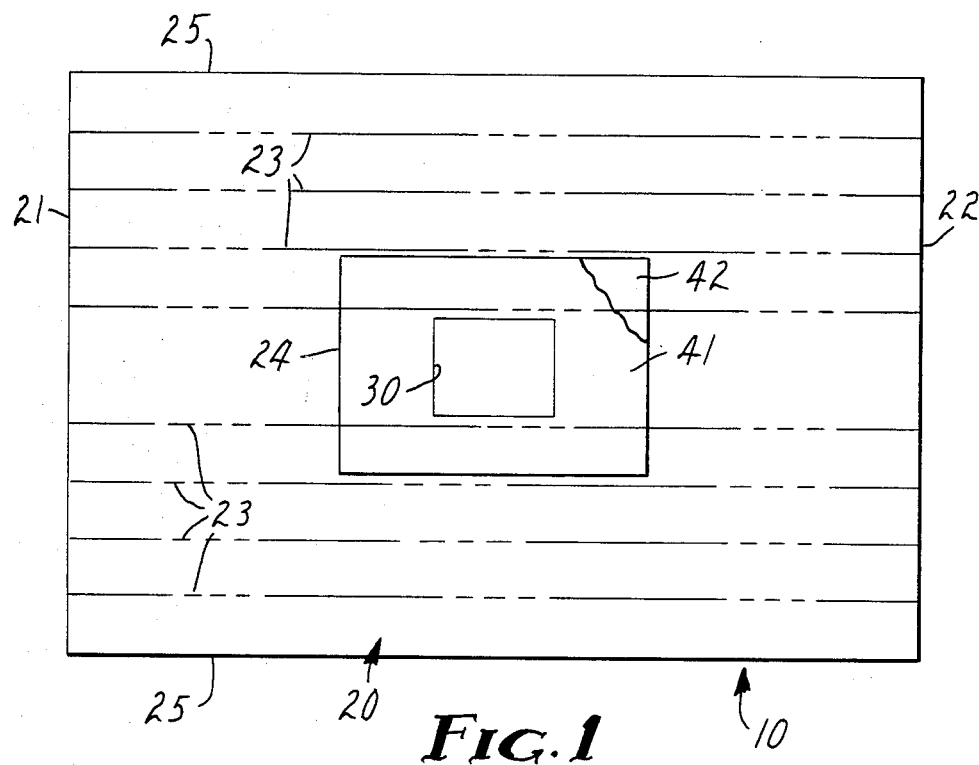
FIG. 1 is a plan view of a draping material with an integrally associated surgical zone showing longitudinal fold lines prior to closing the article into a loop.

Referring now to FIG. 1, the article of the present invention may be conveniently made from a sheet 10 comprised of draping material 20 and a surgical zone 30. The draping material 20 may be any conventional cover sheet material. The material should be capable of being sterilized. It is desirably flexible and fluid repellant or it may have a fluid impervious barrier in its construction. For example the draping material may be fluid absorbent on the surface 27 (shown in FIG. 5) destined to become the patient surface of the drape while the material has a fluid impervious layer 28 preventing wicking of fluids to the layer 29, the outer surface of which is destined to become the upper surface of the drape. Additionally the upper surface is preferably low gloss. Suitable materials include BLUE FABRIC TM (commercially available from 3M Company, St. Paul, Minn.) which is a sandwich laminate of carded rayon webs as the fluid absorbent material and a polyethylene film disposed between the webs as the fluid impervious barrier. This material and the polymeric binding of the webs to the thermoplastic film are more particularly described in U.S. Pat. No. 3,809,077 which is incorporated herein by reference. A preferred material is AS-SURE I TM, a wet-laid composite paper material with fluorochemical treatment manufactured by and available from Dexter Corporation, Conn. Most preferred is SONTARA TM, a mechanically softened spun laced polyester/wood pulp blend manufactured by and available from DuPont, Wilmington, Del. While less preferred because their cost prevents their use as disposable cover sheets, woven draping materials such as LIQUA-SHIELD TM manufactured by and available from Fashion Seal Uniforms, a division of Superior Surgical Mfg., Huntington, N.Y., are suitable. Conventional woven fabrics such as cotton, polyester/cotton blends, and polyesters are also less preferred but nonetheless suitable. Also suitable are extruded films which are commercially available and familiar to those skilled in the art.

The draping material is preferably provided with a reinforcing panel 24. The reinforcing panel is secured to the surface of the draping material that will become the upper surface of the drape in an area surrounding the surgical zone 30. The reinforcing panel serves to reinforce the borders of the surgical zone 30 and to increase and protect the structural integrity of the draping material during surgery. It is desirably fluid absorbent on its exposed surface 41 with a fluid impervious layer preventing migration of fluids through the surface 42 secured to the draping material. The reinforcing panel can be conveniently made from BLUE FABRIC TM (3M Company, St. Paul, Minn.) or a two layer laminate having only one absorbent layer and an impervious film. Any suitable process such as thermal-bonding, sonic sealing, or use of a pressure sensitive or hot-melt adhesive may be used to secure the reinforcing panel to the draping material.

Figure 7:
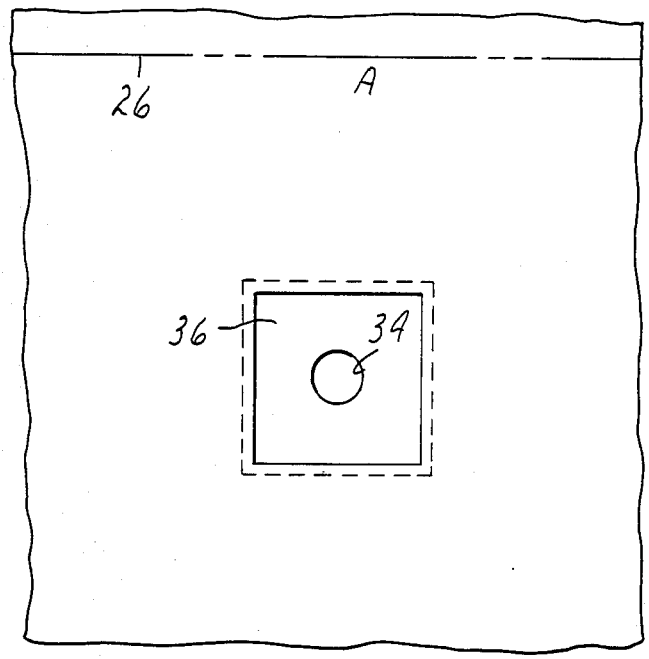
FIG. 7 is a plan view of a portion of the cover sheet showing a stretchy aperture as the surgical zone.

The surgical zone 30 may be a fenestration, incise patch, stretchy aperture comprised of a stretchy film 33 with an aperture 34 (as shown in FIG. 7) or composite of any size and configuration. The surgical zone 30 could even be a slit in the draping material. Preferably the surgical zone is rectangular in shape and has its longitudinal axis positioned equidistant from each of the side edges 25 of the draping material. A preferred surgical zone is an incise patch comprised of a flexible film with an adhesive, preferably a pressure sensitive acrylate adhesive, and a releasable liner 31. Films having high moisture vapor transmission rates which are impervious to liquids are especially preferred. Suitable films include polyurethanes, polyesters, and linear low density polyethylenes. The incise patch may include an antimicrobial agent such as iodophor. An incise patch having an iodophor antimicrobial agent is IOBAN ® 2 Antimicrobial Film commercially available from 3M Company, St. Paul, Minn. Pressure sensitive antimicrobial adhesives 32 and incise composites are more particularly described in U.S. Pat. Nos. 4,310,509 and 4,323,557. U.S. Pat. No. 4,323,557 is incorporated herein by reference. The incise patch is preferably laminated to the draping material 20 by removing the releasable liner from the edges of the pressure sensitive adhesive coated film and placing the film on the upper surface of the reinforcing panel 24 so that the adhesive film overlaps the reinforcing panel and is attached to the panel by means of its own laminating adhesive.

Figure 2:
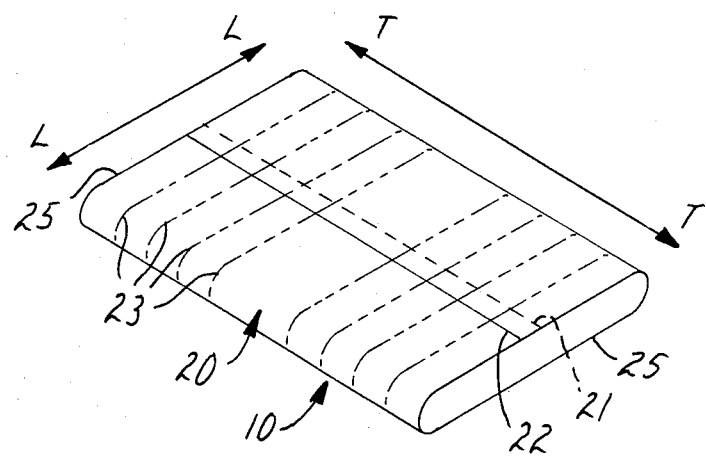
FIG. 2 is a perspective view of the article of the present invention formed as a closed loop.

The draping material with its associated surgical zone may be formed into a closed loop as shown in FIG. 2 by joining the longitudinal ends 21 and 22 of the draping material. The joining may be affected by any suitable means such as taping the ends together or using a transfer adhesive, using a hot melt adhesive, heat sealing the ends, sewing, sonic sealing, and the like.

Also shown in FIGS. 1 and 2 are longitudinal fold lines 23. The transverse dimension of the loop, line T—T of FIG. 2, is preferably reduced by folding the draping material 20 along circumferential longitudinal fold lines 23. Most preferably the longitudinal folds are fan folds from each side edge 25 towards the center resulting in two juxtaposed stacks of longitudinal folds stacked on the inside of the loop.

The loop is also preferably folded to reduce its longitudinal dimension, shown as line L—L in FIG. 2. This reduction of the longitudinal dimension is preferably achieved by folding the loop along transverse fold lines 26 as shown in FIG. 3.

Figure 3:
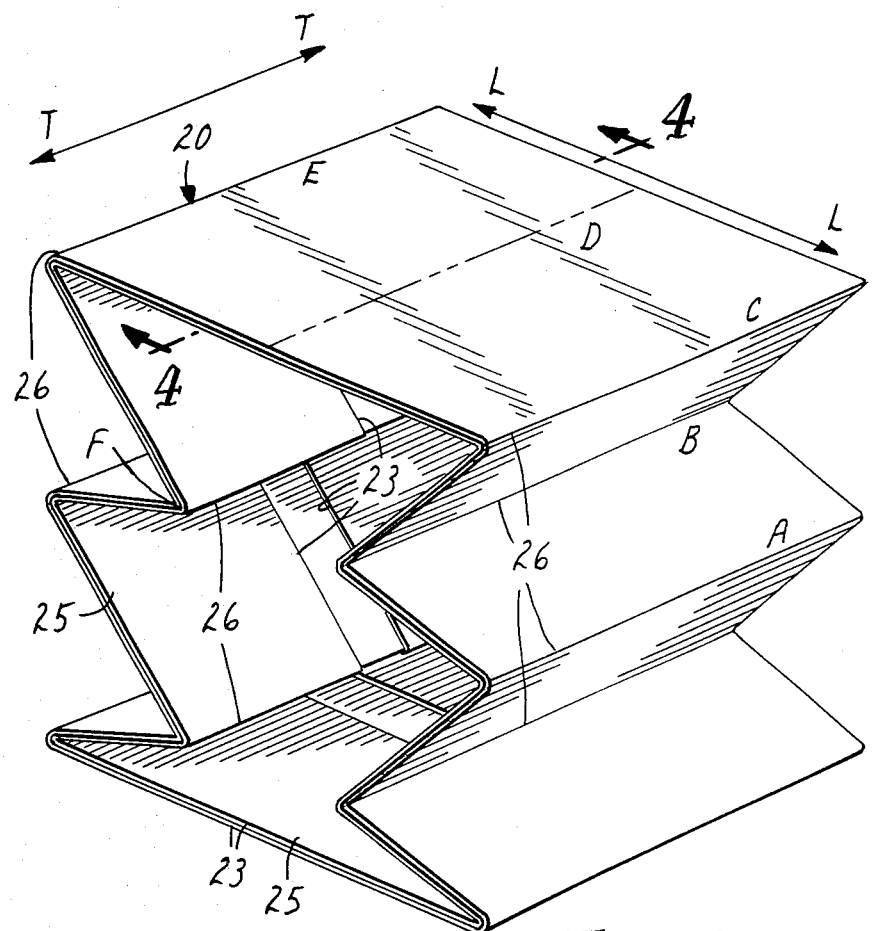
FIG. 3 is an enlarged perspective view of the article of the present invention showing transverse folds and transverse cut lines.
Figure 4:
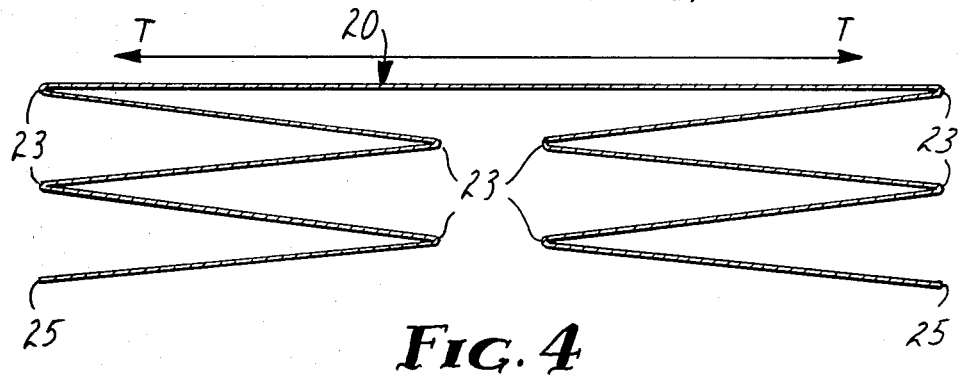
FIG. 4 is an enlarged cross-sectional view taken along section 4—4 of FIG. 3 showing longitudinal folding of the article.

FIGS. 3 and 4 show the most preferred folding pattern for the loop article of the present invention. Preferably the transverse dimension is reduced by fan folds along lines 23 inwardly from each edge of the loop. Thereafter the longitudinal dimension is reduced by fan folds along fold lines 26. Preferably the loop is folded so that the surgical zone is exposed at an outer surface. As shown in FIG. 3 the surgical zone would lie on the bottom of the loop.

Figure 5:
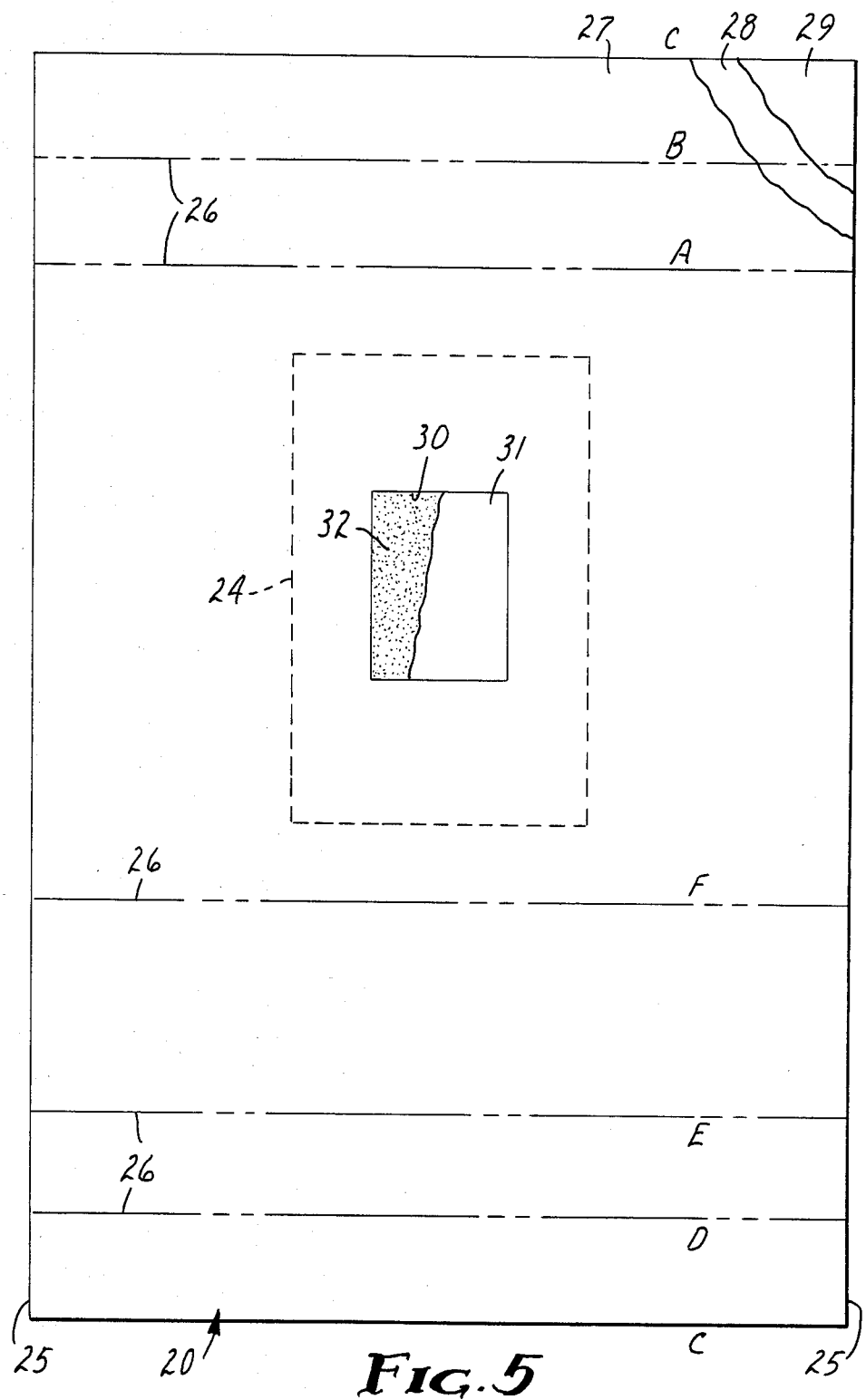
FIG. 5 is plan view of the patient surface article of the present invention after cutting along line "C" of FIG. 3.
Figure 6:
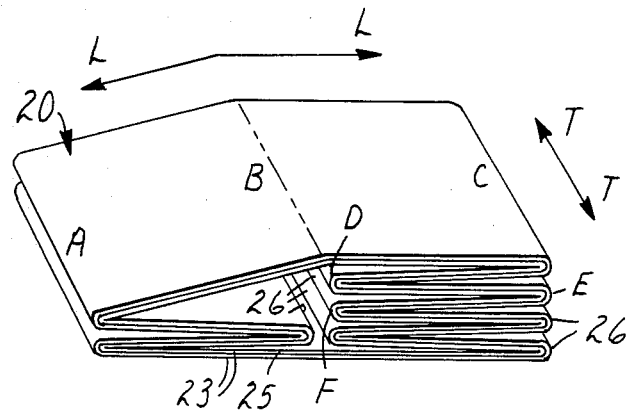
FIG. 6 is a perspective view of the article of the present invention folded for cutting along transverse cut line "B".

In the preferred embodiment, transverse cut labels are marked on the draping material. Most preferably the transverse cut marks fall on transverse fold lines 26. As shown in FIG. 4, cutting a loop sized to yield a full length sheet of conventional cover sheet dimensions, e.g. the article being 72 inches (183 cm) wide and 108 inches (274 cm) long and having a surgical zone measuring 12 inches (30 cm) wide by 16 inches (41 cm) long, along the transverse cut line A would yield a surgical cover sheet having the surgical zone placed appropriately for head/neck surgery. Cutting along transverse cut line B (as shown in FIG. 6) would yield a cover sheet with surgical zone placement suitable for chest surgery. Cutting along transverse cut line C (as shown in FIG. 5) would yield a cover sheet suitable for laparotomies. Cutting along transverse cut line D would yield a cover sheet suitable for hip surgery. Cutting along transverse cut line E would yield a cover sheet having surgical zone placement suitable for knee surgery. Finally, cutting along transverse cut line F would yield a cover sheet suitable for ankle/foot surgery.

In use the sterile nurse would deliver the loop folded as shown in FIGS. 3 and 4 from its package to the sterile back table. When the loop has transverse cut lines placed on fold lines as shown in FIG. 3, the sterile nurse can conveniently turn folds, like turning pages of a book, to find the fold line along which the loop should be cut for the surgical procedure planned. The loop is opened transversely at this point for example by cutting with a scissors, thereby forming a cover sheet with surgical zone positioned within the draping material.

When the loop is opened in this manner adequate draping material is provided for covering the patient during the surgical procedure contemplated when the surgical zone is placed to permit access to the body area involved in the procedure. When the longitudinal folds have been made as shown in FIG. 4 with the first fold from the edge being a reverse fold, that is, the surface destined to become the patient surface of the drape is folded towards itself, a cuff is naturally formed between the upper most and second upper most fan fold segments which allows the circulating nurse to assist in unfolding and insures sterility maintenance in application of the cover sheet. The cover sheet is now ready for application to the patient in the following manner. First the surgical nurse removes the liner from the incise patch and positions the pressure sensitive adhesive area of the incise patch onto the intended incision site of the patient. Alternatively, if the drape has a stretchy aperture the nurse pulls the involved limb through the opening in the stretchy aperture and places the surgical zone at an appropriate point along the limb. Next, the nurse unfolds the cover sheet in the longitudinal direction that is towards the head and foot of the patient. Then the cover sheet can be unfolded in the transverse direction. Finally, where the cover sheet has an incise patch the pressure sensitive adhesive should be firmly smoothed to the patient's skin.

The foregoing description has been directed to the preferred constructions and a method of making and using the article of the present invention. Persons skilled in the art will readily appreciate that a variety of other embodiments are embraced within the invention. For example, the longitudinal folds could be roll folds rather than fan folds. The term roll folds is intended to describe folding patterns of successive forward folds or successive reverse folds a distinguished from a fan folding pattern of alternating forward and reverse folds. Similarly, the folds could progress from one side all the way to the other side rather than from each side to center. The entire loop could be turned inside out. Additional features such as cord organizers, instrument holders, fluid collection pouches, wicking devices, and the like could be incorporated into the construction. While the loop is preferably opened by cutting with sterile scissors, alternatives are available such as use of a tear strip, or removal of a tape. The following claims are intended to embrace all such modifications and variations.

What is claimed is:

1. An article adaptable for draping non-surgical areas of patient and providing a surgical zone during an invasive medical procedure comprising draping material having opposing side edges of substantially equal length and a surgical zone integrally associated with the draping material, the article being formed in a closed loop and being dimensioned such that opening of the loop yields a surgical cover sheet wherein the surgical zone is positioned within the draping material so that non-surgical areas of the patient are covered sufficiently for surgical purposes by draping material when the surgical zone is placed to permit access to the body area involved in the procedure.

2. The article of claim 1 wherein the outer surface of the loop is adapted to become the patient surface of the cover sheet upon opening of the loop.

3. The article of claim 1 wherein the transverse dimension of the article is reduced by longitudinal folding of the draping material.

4. The article of claim 2 wherein the draping material is folded from each side edge inwardly to form two juxtaposed stacks of longitudinal folds stacked on the inside of the closed loop.

5. The article of claim 4 wherein the longitudinal folds are fan folds.

6. The article of claim 4 wherein the surgical zone is substantially rectangular and the longitudinal axis of the surgical zone is substantially equidistant from the side edges of the draping material.

7. The article of claim 3 wherein the longitudinal dimension of the longitudinally folded article has been reduced by transverse folding of the article.

8. The article of claim 1 wherein the draping material is provided with a plurality of transverse cut marks spaced at intervals from the surgical zone to facilitate determination of the transverse line across the draping material at which the loop should be opened to achieve correct positioning of the surgical zone within the draping material for the procedure to be performed.

9. The article of claim 8 wherein the transverse cut marks are spaced at intervals from the surgical zone to facilitate determination of the transverse line along which the loop should be opened to achieve desired positioning of the surgical zone within the draping material for the procedure to be performed.

10. The article of claim 1 wherein the surgical zone is a fenestration.

11. The article of claim 1 wherein the surgical zone is a stretchy aperture.

12. The article of claim 1 wherein the surgical zone is an incise patch comprised of a film, a pressure sensitive adhesive coated on the surface of the film which will form the patient surface of the surgical zone when the loop is opened, and a liner releasably affixed to the adhesive.

13. The article of claim 7 wherein the surgical zone is an incise patch comprised of a film, a pressure sensitive adhesive coated on the surface of the film which will become the patient surface of the surgical zone when the loop is opened, and a liner releasably affixed to the adhesive and the loop is folded to expose the liner at an outer surface of the article to permit removal of the liner and placement of the surgical zone on the surgical site prior to unfolding of the cover sheet.

14. The article of claim 13 wherein the adhesive incorporates an antimicrobial agent.

15. The article of claim 7 wherein the surgical zone is a stretchy aperture and the article is folded to expose the surgical zone at an outer surface of the article to permit placement of the surgical zone on the surgical site prior to unfolding of the cover sheet.

16. An article adaptable for draping non-surgical areas of a patient and providing a surgical zone during an invasive medical procedure comprising draping material having opposing side edges and a surgical zone integrally associated with the draping material, the article being formed as a closed loop and being dimensioned such that transverse opening of the loop yields a medical cover sheet having the surgical zone positioned within the draping material so that non-surgical areas of the patient are covered sufficiently for surgical purposes by draping material when the surgical zone is placed to permit access to the body area involved in the procedure wherein:

the outer surface of the loop is adapted to become the patient surface of the drape upon opening of the loop;

the transverse dimension of the article is reduced by folding of the draping material in fan folds from each side edge inwardly to form two juxtaposed stacks of longitudinal folds stacked on the inside of the loop;

the longitudinal dimension of the loop is reduced by transverse folding of the longitudinally folded article;

the draping material is provided with a plurality of transverse cut marks spaced at intervals from the surgical zone to facilitate determination of the transverse line across the draping material at which the loop should be opened to achieve correct positioning of the surgical zone within the draping material for the procedure to be performed;

the surgical zone is an incise patch having a film, a pressure sensitive adhesive coated on the outer surface of the film, and a liner releasably secured to the adhesive; and the loop is folded to expose the liner at an outer surface to permit removal of the liner and placement of the surgical zone prior to unfolding of the cover sheet.

17. The article of claim 16 wherein the adhesive incorporates an antimicrobial agent.

18. A process for draping a patient for an invasive medical procedure with an article having draping material and an integrally associated surgical zone the article being formed as a closed loop and folded first along annular longitudinal fold lines and thereafter along transverse fold lines circumferentially along the loop with the surgical zone exposed at an outer surface of the folded article comprising in sequential order:

transversely opening the closed loop along a line sufficiently distant from the surgical zone to form a cover sheet wherein the surgical zone is positioned within the draping material so as to provide lengths of draping material between the surgical zone and the respective ends of the cover sheet adequate to sufficiently cover non-surgical areas when the surgical zone is placed to permit access to the body area involved in the procedure;

placing the surgical zone with respect to the patient to permit access to the body area involved in the procedure;

unfolding the transverse folds of draping material; and unfolding the longitudinal folds of draping material.

19. A process for draping a patient for an invasive medical procedure comprising:

providing a closed loop article comprised of draping material and a surgical zone integrally associated with the draping material;

opening the loop along a line distanced an appropriate length from the surgical zone to create a cover sheet with the surgical zone positioned within the draping material between the surgical zone and the respective ends of the cover sheet so as to provide lengths of draping material adequate to sufficiently cover non-surgical areas of the patient when the surgical zone is placed to permit access to the body area involved in the procedure; and positioning the cover with respect to the patient so that the surgical zone is placed to permit access to the body area involved in the procedure and adequately cover the non-surgical areas of the patient.

* * * * *